(12) United States Patent
Pasmooij (10) Patent No.: US 11,468,787 B1
(45) Date of Patent: Oct. 11, 2022

(54) DIABETIC TREATMENT MANAGEMENT SYSTEM

(71) Applicant: Duco B. Pasmooij, Los Altos, CA (US)

(72) Inventor: Duco B. Pasmooij, Los Altos, CA (US)

(73) Assignee: Apple Inc., Cupertino, CA (US)

( * ) Notice: Subject to any disclaimer, the term of this patent is extended or adjusted under 35 U.S.C. 154(b) by 96 days.

(21) Appl. No.: 16/899,152

(22) Filed: Jun. 11, 2020

Related U.S. Application Data

(60) Provisional application No. 62/860,376, filed on Jun. 12, 2019.

(51) Int. Cl.
| | |
|---|---|
| *G09B 19/00* | (2006.01) |
| *A61B 5/00* | (2006.01) |
| *A61B 5/145* | (2006.01) |
| *G06V 20/10* | (2022.01) |
| *G06V 20/68* | (2022.01) |

(52) U.S. Cl.
CPC ...... *G09B 19/0092* (2013.01); *A61B 5/14532* (2013.01); *A61B 5/486* (2013.01); *A61B 5/4839* (2013.01); *A61B 5/4866* (2013.01); *A61B 5/742* (2013.01); *G06V 20/10* (2022.01); *G06V 20/68* (2022.01)

(58) Field of Classification Search
CPC .................................................. G09B 19/0092
See application file for complete search history.

(56) References Cited

U.S. PATENT DOCUMENTS

| | | | |
|---|---|---|---|
| 9,892,501 B2 | 2/2018 | Dehais | |
| 2006/0272652 A1* | 12/2006 | Stocker | ............... G16H 50/50 |
| | | | 128/898 |
| 2011/0124996 A1 | 5/2011 | Reinke | |
| 2017/0173262 A1 | 6/2017 | Veltz | |
| 2017/0220751 A1 | 8/2017 | Davis | |

OTHER PUBLICATIONS

"DreaMed: Advisory" Nov. 4, 2018, Retrieved from the Internet: URL: https://dreadmed-diabetes/advisor/ [Retrieved on Feb. 13, 2019].
"Insulin Management for Kids with Diabetes," The Omnipod System for Kids, Omnipod Insulin Management System, 2018, Retrieved from the Internet: URL: https://www.myomnipod.com/become-a-podder/pediatric [Retrieved on Feb. 13, 2019].
"Medilync—Overview," Retrieved from the Internet: URL: https://www.medilync.com/overview/ [Retrieved on Feb. 13, 2019].

(Continued)

*Primary Examiner* — Kesha Frisby
(74) *Attorney, Agent, or Firm* — Blank Rome LLP (57) ABSTRACT

Providing a treatment adjustment plan for a user based on blood glucose data may include obtaining a user profile comprising health information for a user; obtaining, from a camera, image data capturing a food product in front of the user; and identifying the food product based on the image data. Providing the treatment adjustment plan may also include detecting user consumption of the food product; obtaining blood glucose characteristics associated with the food product; determining an estimated blood glucose response based on the blood glucose characteristics and the user profile; and determining a treatment adjustment based on the estimated blood glucose response.

23 Claims, 7 Drawing Sheets

(56) References Cited

OTHER PUBLICATIONS

Ding, Sandrine, and Michael Schumacher, "Sensor Monitoring of Physical Activity to Improve Glucose Management in Diabetic Patients: A Review," Sensors (Basel), Apr. 16, 2016.
Gu, Shixin, "Deep Learning-Based Food Calorie Estimation Method in Dietary Assessment," Aug. 3, 2017, Retrieved from the Internet: URL: https://medium.com/syncedreview/deep-learning-based-food-calorie-estimation-method-in-dietary-assessment-1e76a2acee7 [Retrieved on Feb. 13, 2019].
Marling, et al., "Emerging Applications for Intelligent Diabetes Management," AI Magazine, vol. 33, No. 2, Mar. 16, 2012.
Ungerlieder, Neal, "Why This Diet App is Using Computer Vision to Help You Lose Weight," Sep. 29, 2016, Retrieved from the Internet: URL: https://www.fastcompany.com/3064074/why-this-diet-apps-using-computer-vision-to-help-you-lose-weight [Retrieved on Feb. 13, 2019].
Zecchin, et al., "Physical Activity Measured by Physical Activity Monitoring System Correlates with Glucose Trends Reconstructed from Continuous Glucose Monitoring," Diabetes Technology & Therapeutics, Oct. 15, 2013.

\* cited by examiner

DIABETIC TREATMENT MANAGEMENT SYSTEM

BACKGROUND

This disclosure relates generally to the field of blood glucose management, and more specifically to the field of blood glucose management in an electronic device.

Many factors contribute to an individual's response to insulin and glucose absorption. For example, some carbohydrates are processed slower or quicker than others, influencing the rate of glucose absorption. Other factors include the individual's activity level, other medications, hormone levels, dehydration, altitude, and other foods eaten. For another example, serving sizes and nutritional information may be difficult to obtain while eating in a restaurant, resulting in inaccurate carbohydrate counts and by extension inaccurate calculations for insulin doses. Because of the highly individualized nature of insulin response and glucose absorption, individuals with diabetes or other medical conditions are often forced to guess what an appropriate insulin dose is. Thus, what is needed is an improved and individualized blood glucose management system.

SUMMARY

In one embodiment, a method for improving blood glucose management is described. A method for improving blood glucose management includes obtaining a user profile, comprising health information for a user; obtaining, by a camera, image data capturing a food product in front of the user; identifying the food product based on image data; detecting user consumption of the food product; obtaining blood glucose characteristics associated with the food product; determining an estimated blood glucose response based on the blood glucose characteristics and the user profile; and determining a treatment adjustment based on the estimated blood glucose response.

In another embodiment, the method may be embodied in computer executable program code and stored in a non-transitory storage device. In yet another embodiment, the method may be implemented in an electronic device having image capture capabilities.

DETAILED DESCRIPTION

This disclosure is directed to systems, methods, and computer readable media for determining treatment adjustments. In general, techniques are disclosed to improve blood glucose management. According to one or more embodiments, improving blood glucose management may allow a person to keep a blood glucose level within acceptable limits.

According to one or more embodiments, a camera may capture an image of a food product. For example, the camera may take a picture of a sandwich and chips. A treatment adjustment may be determined by identifying the food product as a sandwich and chips, detecting user consumption of the sandwich and chips, obtaining a user profile including health information for a user and blood glucose characteristics for the sandwich and chips, determining an estimated blood glucose response based on the blood glucose characteristics and the user profile, and determining a treatment adjustment based on the estimated blood glucose response. In one or more embodiments, the determination of a treatment adjustment may be more accurate than traditional methods of treatment adjustment. Thus, when food consumption is detected, the user may keep blood glucose levels within acceptable limits.

In the following description, for purposes of explanation, numerous specific details are set forth in order to provide a thorough understanding of the disclosed concepts. As part of this description, some of this disclosure's drawings represent structures and devices in block diagram form in order to avoid obscuring the novel aspects of the disclosed embodiments. In this context, it should be understood that references to numbered drawing elements without associated identifiers (e.g., 100) refer to all instances of the drawing element with identifiers (e.g., 100a and 100b). Further, as part of this description, some of this disclosure's drawings may be provided in the form of a flow diagram. The boxes in any particular flow diagram may be presented in a particular order. However, it should be understood that the particular flow of any flow diagram is used only to exemplify one embodiment. In other embodiments, any of the various components depicted in the flow diagram may be deleted, or the components may be performed in a different order, or even concurrently. In addition, other embodiments may include additional steps not depicted as part of the flow diagram. The language used in this disclosure has been principally selected for readability and instructional purposes, and may not have been selected to delineate or circumscribe the disclosed subject matter. Reference in this disclosure to "one embodiment" or to "an embodiment" means that a particular feature, structure, or characteristic described in connection with the embodiment is included in at least one embodiment, and multiple references to "one embodiment" or to "an embodiment" should not be understood as necessarily all referring to the same embodiment or to different embodiments.

It should be appreciated that in the development of any actual implementation (as in any development project), numerous decisions must be made to achieve the developers' specific goals (e.g., compliance with system and business-related constraints), and that these goals will vary from one implementation to another. It will also be appreciated that such development efforts might be complex and time consuming, but would nevertheless be a routine undertaking for those of ordinary skill in the art having the benefit of this disclosure.

For purposes of this disclosure, the term "microphone" refers to a transducer that converts sound into an electrical signal. In one or more embodiments, the microphone may refer to any kind of microphone, such as a dynamic microphone, a condenser microphone, or a piezoelectric microphone. Further in one or more embodiments, the microphone may be an internal component of an electronic device or a separate external component connected to an electronic device at will by a user.

For purposes of this disclosure, the term "camera" refers to a lens assembly along with the sensor element and other circuitry utilized to capture an image. In one or more embodiments, the lens assembly may include multiple lenses. Further in one or more embodiments, the lens may be moved to various positions to capture images at multiple depths and, as a result, multiple points of focus. In one or more embodiments, the lens may refer to any kind of lens, such as a telescopic lens or a wide angle lens. As such, the lens assembly can mean a single optical element or multiple elements configured into a stack or other arrangement.

For purposes of this disclosure, the term "glucose monitor" refers to a device that measures and outputs a blood glucose measurement for an individual. In one or more embodiments, the glucose monitor may refer to any kind of glucose monitor, such as a continuous glucose monitor, a non-invasive glucose monitor, or a conventional finger-prick glucose monitor. Further in one or more embodiments, the glucose monitor may be an internal component of an electronic device or a separate external component connected to an electronic device at will by a user.

For purposes of this disclosure, the term "insulin administration device" refers to a device that administers insulin to a user. In one or more embodiments, the insulin administration device may refer to any kind of insulin administration device, such as an insulin pump, an insulin pen, or an insulin syringe. Further in one or more embodiments, the insulin administration device may be a separate external component connected to an electronic device at will by a user.

A physical setting refers to a world that individuals can sense and/or with which individuals can interact without assistance of electronic systems. Physical settings (e.g., a physical forest) include physical elements (e.g., physical trees, physical structures, and physical animals). Individuals can directly interact with and/or sense the physical setting, such as through touch, sight, smell, hearing, and taste.

In contrast, a simulated reality (SR) setting refers to an entirely or partly computer-created setting that individuals can sense and/or with which individuals can interact via an electronic system. In SR, a subset of an individual's movements is monitored, and, responsive thereto, one or more attributes of one or more virtual objects in the SR setting is changed in a manner that conforms with one or more physical laws. For example, a SR system may detect an individual walking a few paces forward and, responsive thereto, adjust graphics and audio presented to the individual in a manner similar to how such scenery and sounds would change in a physical setting. Modifications to attribute(s) of virtual object(s) in a SR setting also may be made responsive to representations of movement (e.g., audio instructions).

An individual may interact with and/or sense a SR object using any one of his senses, including touch, smell, sight, taste, and sound. For example, an individual may interact with and/or sense aural objects that create a multi-dimensional (e.g., three dimensional) or spatial aural setting, and/or enable aural transparency. Multi-dimensional or spatial aural settings provide an individual with a perception of discrete aural sources in multi-dimensional space. Aural transparency selectively incorporates sounds from the physical setting, either with or without computer-created audio. In some SR settings, an individual may interact with and/or sense only aural objects.

One example of SR is virtual reality (VR). A VR setting refers to a simulated setting that is designed only to include computer-created sensory inputs for at least one of the senses. A VR setting includes multiple virtual objects with which an individual may interact and/or sense. An individual may interact and/or sense virtual objects in the VR setting through a simulation of a subset of the individual's actions within the computer-created setting, and/or through a simulation of the individual or his presence within the computer-created setting.

Another example of SR is mixed reality (MR). A MR setting refers to a simulated setting that is designed to integrate computer-created sensory inputs (e.g., virtual objects) with sensory inputs from the physical setting, or a representation thereof. On a reality spectrum, a mixed reality setting is between, and does not include, a VR setting at one end and an entirely physical setting at the other end.

In some MR settings, computer-created sensory inputs may adapt to changes in sensory inputs from the physical setting. Also, some electronic systems for presenting MR settings may monitor orientation and/or location with respect to the physical setting to enable interaction between virtual objects and real objects (which are physical elements from the physical setting or representations thereof). For example, a system may monitor movements so that a virtual plant appears stationery with respect to a physical building.

One example of mixed reality is augmented reality (AR). An AR setting refers to a simulated setting in which at least one virtual object is superimposed over a physical setting, or a representation thereof. For example, an electronic system may have an opaque display and at least one imaging sensor for capturing images or video of the physical setting, which are representations of the physical setting. The system combines the images or video with virtual objects, and displays the combination on the opaque display. An individual, using the system, views the physical setting indirectly via the images or video of the physical setting, and observes the virtual objects superimposed over the physical setting. When a system uses image sensor(s) to capture images of the physical setting, and presents the AR setting on the opaque display using those images, the displayed images are called a video pass-through. Alternatively, an electronic system for displaying an AR setting may have a transparent or semi-transparent display through which an individual may view the physical setting directly. The system may display virtual objects on the transparent or semi-transparent display, so that an individual, using the system, observes the virtual objects superimposed over the physical setting, in another example, a system may comprise a projection system that projects virtual objects into the physical setting. The virtual objects may be projected, for example, on a physical surface or as a holograph, so that an individual, using the system, observes the virtual objects superimposed over the physical setting.

An augmented reality setting also may refer to a simulated setting in which a representation of a physical setting is altered by computer-created sensory information. For example, a portion of a representation of a physical setting may be graphically altered (e.g., enlarged), such that the altered portion may still be representative of but not a faithfully-reproduced version of the originally captured image(s). For another example, in providing video pass-through, a system may alter at least one of the sensor images to impose a particular viewpoint different than the viewpoint captured by the image sensor(s). As an additional example, a representation of a physical setting may be altered by graphically obscuring or excluding portions thereof.

Another example of mixed reality is augmented virtuality (AV). An AV setting refers to a simulated setting in which a computer-created or virtual setting incorporates at least one sensory input from the physical setting. The sensory input(s) from the physical setting may be representations of at least one characteristic of the physical setting. For example, a virtual object may assume a color of a physical element captured by imaging sensor(s). In another example, a virtual object may exhibit characteristics consistent with actual weather conditions in the physical setting, as identified via imaging, weather-related sensors, and/or online weather data. In yet another example, an augmented reality forest may have virtual trees and structures, but the animals may have features that are accurately reproduced from Images taken of physical animals.

Figure 1:
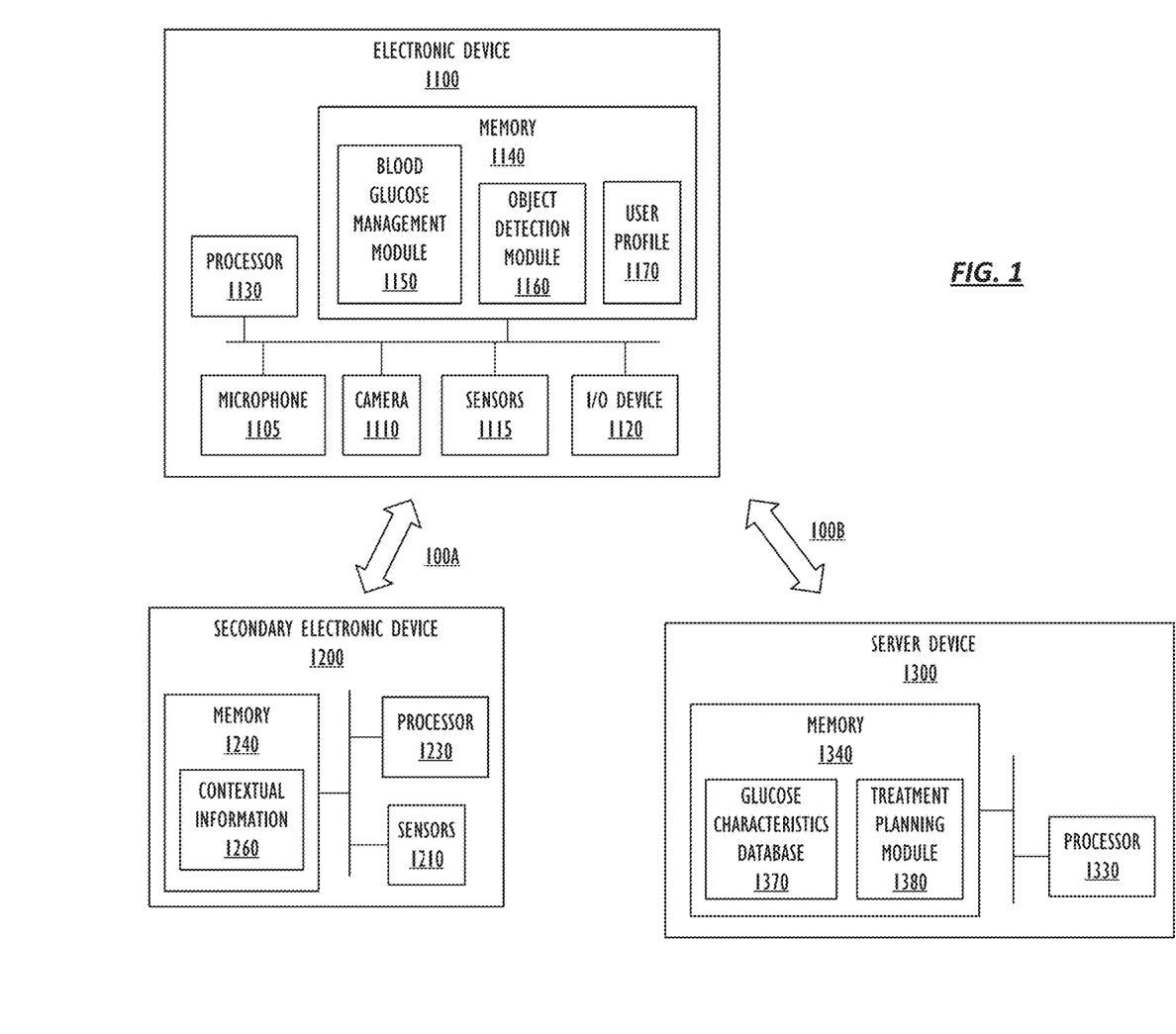
FIG. 1 shows, in block diagram form, a simplified electronic device, a secondary electronic device, and a server device, according to one or more embodiments.

FIG. 1 shows, in block diagram form, an overall view of a system diagram capable of supporting improved blood glucose management, according to one or more embodiments. Specifically, FIG. 1 depicts an electronic device 1100 that is a computer system. Electronic device 1100 may be part of a multifunctional device, such as a mobile phone, tablet computer, personal digital assistant, or a wearable device. Electronic device 1100 may be connected to other devices across a network, such as secondary electronic device 1200, mobile devices, tablet devices, desktop devices, glucose monitors, and insulin administration devices, as well as network storage devices such as server device 1300 and the like. Electronic device 1100 may also be connected to secondary electronic device 1200 via a wireless, or a wired connection. FIG. 1 shows connection 100A between electronic device 1100 and secondary electronic device 1200 and connection 100B between electronic device 1100 and server device 1300. Connections 100A and 100B need not be the same type of connection and may each be a network connection, a wired connection, or a Bluetooth connection, among others.

Electronic device 1100 may include a processor 1130. Processor 1130 may be a system-on-chip such as those found in mobile devices and include one or more central processing units (CPUs), dedicated graphics processing units (GPUs), or both. Further processor 1130 may include multiple processors of the same or different type. Electronic device 1100 may also include a memory 1140. Memory 1140 may include one or more different types of memory, which may be used for performing device functions in conjunction with processor 1130. For example, memory 1140 may include cache, ROM, and/or RAM. Memory 1140 may store various programming modules during execution, including blood glucose management module 1150, object detection module 1160, and a user profile 1170. In one or more embodiments, memory 1140 may also include contextual information 1260.

Electronic device 1100 may include one or more microphones, such as microphone 1105. Microphone 1105 may include a diaphragm and an analog to digital converter. In one or more embodiments, microphone 1105 may detect a chewing noise from a user indicating the user is eating. For example, processor 1130 may obtain the audio data for the chewing session captured by microphone 1105 and determine frequency and amplitude data in the audio data. Processor 1130 may then detect the chewing noise based on the frequency and amplitude data.

Electronic device 1100 may also include one or more cameras, such as camera 1110. Camera 1110 may include an image sensor, a lens stack, and other components that may be used to capture images. For example, camera 1110 may be configured to capture images of an environment from the point of view of a user. In addition, camera 1110 may include multiple cameras, configured to capture images from different points of view. For example, one or more cameras may be front-facing cameras and one or more cameras may be back facing cameras. Electronic device 1100 may also include additional sensors 1115. For example, sensors 1115 may include a glucose monitor or an altimeter.

In one or more embodiments, the electronic device 1100 may also include input/output (I/O) device 1120. I/O device 1120 may be any kind of input or output device, such as microphones for voice control input, speakers for audio data output, cameras for visual input, displays for visual data output, touch screens for tactile input, or any combination thereof. For example, I/O device 1120 may be any kind of display device, such as an LCD display, LED display, OLED display, or the like. Further, the display device may be a traditional display or a semi-opaque display, such as a heads-up display or the like. Further, the display may be part of a head-mounted device (HMD), according to one or more embodiments.

Electronic device 1100 may allow a user to interact with SR environments. Many electronic systems enable an individual to interact with and/or sense various SR settings. One example includes head mounted systems. A head mounted system may have an opaque display and speaker(s). Alternatively, a head mounted system may be designed to receive an external display (e.g., a smartphone). The head mounted system may have imaging sensor(s) and/or microphones for taking images/video and/or capturing audio of the physical setting, respectively. A head mounted system also may have a transparent or semi-transparent display. The transparent or semi-transparent display may incorporate a substrate through which light representative of images is directed to an individual's eyes. The display may incorporate LEDs, OLEDs, a digital light projector, a laser scanning light source, liquid crystal on silicon, or any combination of these technologies. The substrate through which the light is transmitted may be a light waveguide, optical combiner, optical reflector, holographic substrate, or any combination of these substrates. In one embodiment, the transparent or semi-transparent display may transition selectively between an opaque state and a transparent or semi-transparent state. In another example, the electronic system may be a projection-based system. A projection-based system may use retinal projection to project images onto an individual's retina. Alternatively, a projection system also may project virtual objects into a physical setting (e.g., onto a physical surface or as a holograph). Other examples of SR systems include heads up displays, automotive windshields with the ability to display graphics, windows with the ability to display graphics, lenses with the ability to display graphics, headphones or earphones, speaker arrangements, input mechanisms (e.g., controllers having or not having haptic feedback), tablets, smartphones, and desktop or laptop computers.

Although electronic device 1100 is depicted as comprising the numerous components described above, in one or more embodiments, the various components may be distributed across multiple devices as part of a distributed system.

Further, additional components may be used and some of the functionality of any of the components may be combined.

In one or more embodiments, blood glucose management module 1150 is configured to determine a treatment adjustment for a user. For example, the blood glucose management module 1150 may be used to determine a treatment adjustment based on an estimated blood glucose response to a food product. The food product may be identified in any number of ways. For example, in one or more embodiments blood glucose management module 1150 may work in conjunction with object detection module 1160 and camera 1110 to identify the food product. In one or more embodiments, blood glucose management module 1150 may then detect user consumption of the food product in conjunction with microphone 1105, camera 1110, sensors 1115, or some combination thereof. Blood glucose management module 1150 may then obtain blood glucose characteristics associated with the food product, for example from glucose characteristics database 1370. In one or more embodiments, glucose characteristics database 1370 is configured to store historic blood glucose measurement data associated with the food product for one or more additional users and in some embodiments, anonymized health information for the one or more additional users. For example, glucose characteristics database 1370 includes an additional user's age, weight, and gender, as well as a blood glucose measurement for the additional user and a particular food product.

Then, blood glucose management module 1150 determines an estimated blood glucose response based on the blood glucose characteristics of the food product and an obtained user profile including health information for the user, for example user profile 1170. In one or more embodiments, user profile 1170 is configured to store health information for the user, such as age, height, weight, and other health information affecting the user's insulin response and glucose absorption. In one or more embodiments, user profile 1170 includes a medication list, a food log, hormone information, historic blood glucose measurement data for the user, types of insulin available to the user, and insulin administration devices available to the user. For example, the hormone information may indicate the user is a child and prompt blood glucose management module 1150 to account for the growth hormones associated with the child's stage of growth. In one or more further embodiments, user profile 1170 also indicates the user has access to a glucagon formulation administered by a glucagon pump, similar to insulin and insulin pumps. Blood glucose management module 1150 may then determine a treatment adjustment based on the insulin and the insulin pump, and the glucagon and the glucagon pump. For example, blood glucose management module 1150 may determine a glucagon dose to be administered in response to determining the estimated blood glucose response is below a first predetermined threshold, or an insulin dose to be administered in response to determining the estimated blood glucose response is above a second predetermined threshold. In embodiments where blood glucose management module 1150 obtains health information stored in user profile 1170, blood glucose management module 1150 may first obtain the user's informed consent to access user profile 1170. In embodiments where blood glucose management module 1150 is configured to directly implement changes to the insulin pump and the glucagon pump, blood glucose management module 1150 may maintain the user's blood glucose levels within a predetermined range without requiring constant user intervention. Blood glucose management module 1150 then determines a treatment adjustment based on the estimated blood glucose response, and in some embodiments presents a notification based on the determined treatment adjustment through I/O device 1120. The treatment adjustment, estimated blood glucose response, and determined food consumption may be considered health data for the user, subject to federal and/or state laws such as the Health Insurance Portability and Accountability Act (HIPAA). Blood glucose management module 1150 may implement appropriate privacy protections to secure the generated health data and require the user's informed permission to share the generated health data with others.

In one or more embodiments, blood glucose management module 1150 identifies the food product by obtaining location information associated with the image data. For example, blood glucose management module 1150 receives a global positioning system (GPS) location for the location the image data was captured at, for example from a GPS locator included in sensors 1115, and determines a restaurant is at the location. For another example, camera 1110 may continuously obtain images and object detection module 1160 may identify a restaurant name on a menu in an image from camera 1110. The identified restaurant name may prompt object detection module 1160 and processor 1130 to use the restaurant's menu to identify the food product. Blood glucose management module 1150 then communicates with a database containing nutritional information for food products served at the restaurant. In some embodiments, blood glucose management module 1150 obtains blood glucose characteristics associated with the food product by obtaining historic blood glucose measurement data associated with the food product for one or more anonymized additional users. For example, blood glucose management module 1150 communicates with a crowd-sourced database containing other users' anonymized blood glucose measurements associated with the food product, such as glucose characteristics database 1370. In some embodiments, blood glucose management module 1150 determines the one or more additional users satisfy a similarity criterion with the user before including their blood glucose measurements in the blood glucose characteristics associated with the food product. For example, blood glucose management module 1150 determines the one or more additional users are a similar age, weight, and gender as the user. For another example, blood glucose management module 1150 determines the one or more additional users have historical blood glucose measurements indicating similar blood glucose responses to food products as the user, even where the additional users are dissimilar ages, weights, and genders as the user.

In some embodiments, a treatment planning module 1380 determines treatment plans for the food product based on the crowd-sourced blood glucose measurements associated with the food product included in glucose characteristics database 1370. In some embodiments, glucose characteristics database 1370 includes treatment adjustments additional users made after eating the food product. Treatment planning module 1380 may compare the treatment adjustments and determine which treatment adjustments were made most often by additional users. For example, treatment planning module 1380 may determine that a threshold number of additional users made a particular treatment adjustment based on the blood glucose measurement associated with the food product. In some embodiments, treatment planning module 1380 may determine different treatment plans based on anonymized health information for the one or more additional users whose blood glucose measurements are included in glucose characteristics database 1370. For example, treatment planning module 1380 may determine a first set of additional users of a particular age, weight, and gender are associated with a first range of blood glucose measurements associated with the food product and a first treatment adjustment, while a second set of additional users of a different age, weight, and gender are associated with a second range of blood glucose measurements associated with the food product and a second treatment adjustment. Blood glucose management module 1150 may work in conjunction with treatment planning module 1380 to obtain blood glucose characteristics associated with the food product relevant to the user based on user profile 1170. Blood glucose management module 1150 may further determine a treatment adjustment for the user based on the treatment adjustments determined by treatment planning module 1380.

In one or more embodiments, blood glucose management module 1150 determines a treatment adjustment by obtaining a blood glucose measurement for the user from a glucose monitor and obtaining contextual information, for example from contextual information 1260. In some embodiments, contextual information 1260 includes the user's activity level, altitude, and schedule, and may be aggregated from one or more sensors or electronic devices. For example, blood glucose management module 1150 obtains the user's activity level from a heart rate monitor for the user and obtains the user's altitude from an altimeter included in sensors 1115. For another example, blood glucose management module 1150 obtains the user's activity level from object detection module 1160, which determines the user has entered a gym or put on running shoes from an image from camera 1110. For another example, blood glucose management module 1150 obtains the user's schedule from a calendar application included in memory 1140 to determine a user's expected activity level or expected altitude for a certain period of time after the current time. Blood glucose management module 1150 determines a treatment adjustment further based on the blood glucose measurement and the user's current and expected activity level and altitude. In embodiments where blood glucose management module 1150 obtains contextual information 1260, blood glucose management module 1150 may first obtain the user's informed consent to access contextual information 1260 from the one or more sensors or electronic devices.

In one or more embodiments, blood glucose management module 1150 determines a treatment adjustment by determining an adjustment to an insulin treatment. In some embodiments, the adjustment to the insulin treatment is determined based on the estimated blood glucose response, the blood glucose measurement, contextual information 1260, user profile 1170, or some combination thereof. In one or more embodiments, blood glucose management module 1150 determines a treatment adjustment by determining a recommended user action. In some embodiments, the recommended user action is determined based on the estimated blood glucose response, the blood glucose measurement, contextual information 1260, user profile 1170, or some combination thereof. In one embodiment, blood glucose management module 1150 determines the recommended user action by obtaining blood glucose characteristics for a food product, for example a food product listed in user profile 1170 as the user's emergency blood sugar snack. Blood glucose management module 1150 then determines an estimated blood glucose response to the food product. In some embodiments, blood glucose management module 1150 determines the estimated blood glucose response to the food product based on the blood glucose characteristics, user profile 1170, a blood glucose measurement, contextual information 1260, or some combination thereof. Blood glucose management module 1150 then determines a recommended amount of the food product for the user to consume, for example an amount of the food product determined to cause the estimated blood glucose response to be within acceptable blood glucose limits. In some embodiments, blood glucose management module 1150 determines an estimated rate of change in the user's blood glucose levels based on the estimated blood glucose response, the blood glucose measurement, contextual information 1260, user profile 1170, or some combination thereof. Blood glucose management module 1150 then compares the estimated rate of change in the user's blood glucose levels to a first predetermined threshold, and compares the estimated blood glucose response and the blood glucose measurement to a second predetermined threshold. In response to the estimated rate of change in the user's blood glucose levels being greater than the first predetermined threshold and the estimated blood glucose response being less than the second predetermined threshold, blood glucose management module 1150 determines a recommended amount of glucagon for the user to administer in order to avoid dangerously low blood glucose levels. In some embodiments, blood glucose management module 1150 presents a notification based on the determined amount of the food product or determined amount of glucagon through I/O device 1120.

In one or more embodiments, blood glucose management module 1150 detects the user has finished eating the food product. Then, blood glucose management module 1150 obtains a blood glucose measurement for the user and compares the blood glucose measurement to the estimated blood glucose response. Blood glucose management module 1150 determines an additional treatment adjustment based on the blood glucose measurement. In some embodiments, the additional treatment adjustment may be a change to a basal insulin administration rate for the user, for example decreasing the amount of insulin administered over a longer period of time while the user is sleeping. In some embodiments, blood glucose management module 1150 presents a notification based on the additional treatment adjustment through I/O device 1120. In some embodiments, blood glucose management module 1150 then modifies user profile 1170 based on the comparison of the blood glucose measurement and the estimated blood glucose response.

In one or more embodiments, object detection module 1160 is configured to identify a food product based on image data capturing the food product. For example, in one or more embodiments object detection module 1160 may work in conjunction with camera 1110 to obtain image data capturing the food product and identify the food product using a machine learning algorithm. In one or more embodiments, object detection module 1160 may also obtain location information associated with the image data and identify the food product based at least in part on the location information. For example, location information associated with the image data may indicate a particular restaurant, prompting object detection module 1160 and processor 1130 to use the restaurant's menu to identify the food product.

FIG. 1 also shows secondary electronic device 1200 connected to electronic device 1100. Secondary electronic device 1200 may be a mobile device, a tablet, a smartwatch, goggles, insulin administration device, or the like. In one or more embodiments, secondary electronic device 1200 comprises sensors 1210, processor 1230, and memory 1240. In one or more embodiments, sensors 1210 may include a glucose monitor or other sensors utilized to measure the effect of consumption of food or drink on a body, such as blood glucose levels. In one or more embodiments, sensors 1210 may include a heart rate monitor or other sensors utilized to measure an activity level of a user. Processor 1230 may be a system-on-chip such as those found in mobile devices and include one or more central processing units (CPUs), dedicated graphics processing units (GPUs), or both. Further processor 1230 may include multiple processors of the same or different type. Electronic device 1200 may also include a memory 1240. Memory 1240 may include one or more different types of memory, which may be used for storing computer readable code to perform device functions in conjunction with processor 1230. For example, memory 1240 may include cache, ROM, and/or RAM. Memory 1240 may store various programming modules during execution, including contextual information 1260.

FIG. 1 also shows server device 1300 connected to electronic device 1100. Server device 1300 may be any suitable computing device including, for example, an application server and a web server which hosts websites accessible by electronic device 1100. Processor 1330 may be a system-on-chip such as those found in mobile devices and include one or more central processing units (CPUs), dedicated graphics processing units (GPUs), or both. Further processor 1330 may include multiple processors of the same or different type. Server device 1300 may also include a memory 1340. Memory 1340 may include one or more different types of memory, which may be used for storing computer readable code to perform device functions in conjunction with processor 1330. For example, memory 1340 may include cache, ROM, and/or RAM. Memory 1340 may store various programming modules during execution, including glucose characteristics database 1370 and treatment planning module 1380.

Figure 2:
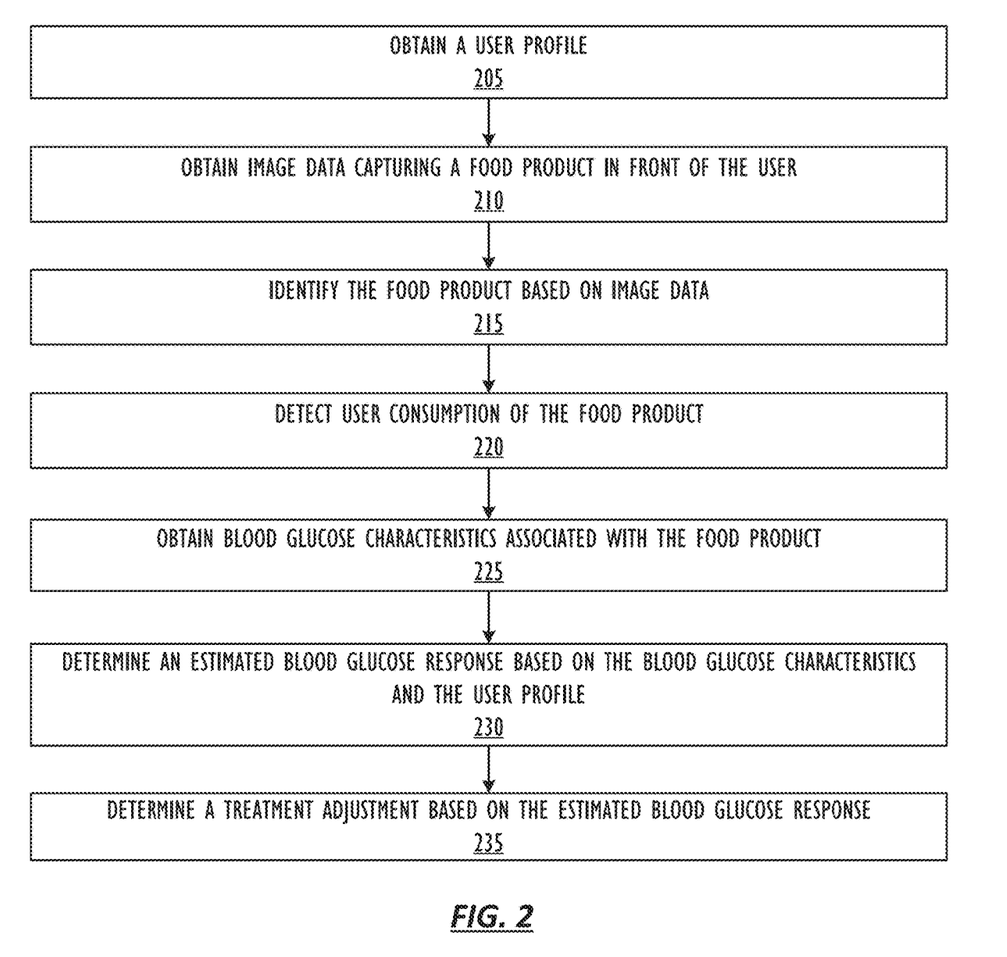
FIG. 2 shows, in flow chart form, a method for improving blood glucose management, according to one or more embodiments.

FIG. 2 shows, in flow chart form, a method for improving blood glucose management. For purposes of explanation, the following steps will be described in the context of FIG. 1. However, it should be understood that the various actions may be taken by alternate components. In addition, the various actions may be performed in a different order. Further, some actions may be performed simultaneously, and some may not be required, or others may be added, according to various embodiments. The flow chart begins at 205, where blood glucose management module 1150 obtains user profile 1170. The flow chart continues at 210, where blood glucose management module 1150 obtains image data capturing a food product in front of the user, such as from camera 1110. The image data may include a still image, a video stream, a series of frames, a live image, or the like. Further, in one or more embodiments, the image data may include location data.

The flow chart continues at 215, where blood glucose management module 1150 identifies the food product based on image data. In one or more embodiments, blood glucose management module 1150 may work in conjunction with object detection module 1160 to identify the food product. For example, object detection module 1160 may use a machine learning algorithm to identify the food product, as discussed previously. In one or more embodiments, blood glucose management module 1150 may also obtain location information associated with the image data and identify the food product based at least in part on the location information.

In one or more embodiments, blood glucose management module 1150 may obtain depth information from the electronic device 1100, or other device, regarding the food product. For example, electronic device 1100 may include a depth camera or other type of sensor or set of sensors which may be used to determine depth. According to one or more embodiments, the object detection module 1160 may determine characteristics of the food product based on the depth information. For example, by determining a detected depth or set of depths of the food product, and an apparent size from the perspective of the electronic device 1100, an estimated size and/or amount of the food product may be determined, which may be used to detect user consumption of the food product or a cessation of user consumption.

In one or more embodiments, the electronic device 1100 may include a microphone 1105 which may capture a recording of the user's speech. In one or more embodiments, recorded conversation or other description may be utilized to refine the object detection to identify the food product. As an example, the object detection module 1160 may register the user saying "this chicken is good!" and thus determine that the food product includes chicken. In one or more embodiments, the voice of the user may provide contextual clues regarding the food product by which the object detection module 1160 can better identify the food product. As an example, a user may say, "Which dressing would you like?" The object detection module may detect the word "dressing" as being related to a salad, for example, or a holiday meal that may include multiple kinds of dressings.

According to one or more embodiments, the object detection module 1160 may record a food preparation process. As a simple example, the object detection module 1160 may better understand the components of a sandwich by tracking the ingredients of the sandwich as it is being constructed. The electronic device 1100 may then store characteristics of the sandwich in a food bank, in local storage and/or in remote storage, such as network storage.

At 220, blood glucose management module 1150 detects user consumption of the food product. Blood glucose management module 1150 may work in conjunction with the microphone 1105, camera 1110, sensors 1115, or some combination thereof. In one or more embodiments, for example, microphone 1105 may be used to detect cessation of user chewing. Additionally, or alternatively, in another embodiment sensors 1115 may comprise a vibrational sensor attached to a user's throat to detect how frequently the user swallows. In addition, in one or more embodiments, characteristics of the chewing session may be analyzed to determine other characteristics of the food, such as an amount of food in the mouth during the chewing session, a texture of the food, and the like. In another embodiment, camera 1110 may be used to capture additional image data of the food product to detect changes in the food product between the image data and the additional image data. For example, the image data of the food product shows six apple slices while the additional image data shows only three apple slices, indicating the user ate three apple slices. In another embodiment, camera 1110 may be oriented towards the user's jaw and movement of the user's jaw may be used to detect user consumption of the food product.

The flow chart continues at 225, where blood glucose management module 1150 obtains blood glucose characteristics associated with the food product. In one or more embodiments, blood glucose management module 1150 may obtain blood glucose characteristics from glucose characteristics database 1370. Note that glucose characteristics database 1370 may be stored in memory 1140 of electronic device 1100 or memory 1340 of server device 1300. Additionally, or alternatively, in one or more embodiments obtaining blood glucose characteristics may include obtaining historic blood glucose measurement data associated with the food product and one or more additional users. For example, the blood glucose characteristics may work in conjunction with treatment planning module 1380 to utilize an anonymized version of additional user blood glucose characteristics to glean potential effects from a particular user consuming certain food products.

At 230, blood glucose management module 1150 determines an estimated blood glucose response based on the blood glucose characteristics and user profile 1170. In one or more embodiments, user profile 1170 may include the user's past recorded blood glucose responses to the food product. Further, in one or more embodiments, determining an estimated blood glucose response is further based on contextual information for the user such as from contextual information 1260, where context information may include at least time of day, temperature, sleep patterns, location, or combinations thereof.

The flow chart ends after 235, where blood glucose management module 1150 determines a treatment adjustment based on the estimated blood glucose response. In some embodiments, the treatment adjustment includes an adjustment to an insulin treatment. In other embodiments, the treatment adjustment includes a recommended user action. In some embodiments, blood glucose management module 1150 then presents a notification based on the treatment adjustment.

Figure 3A:
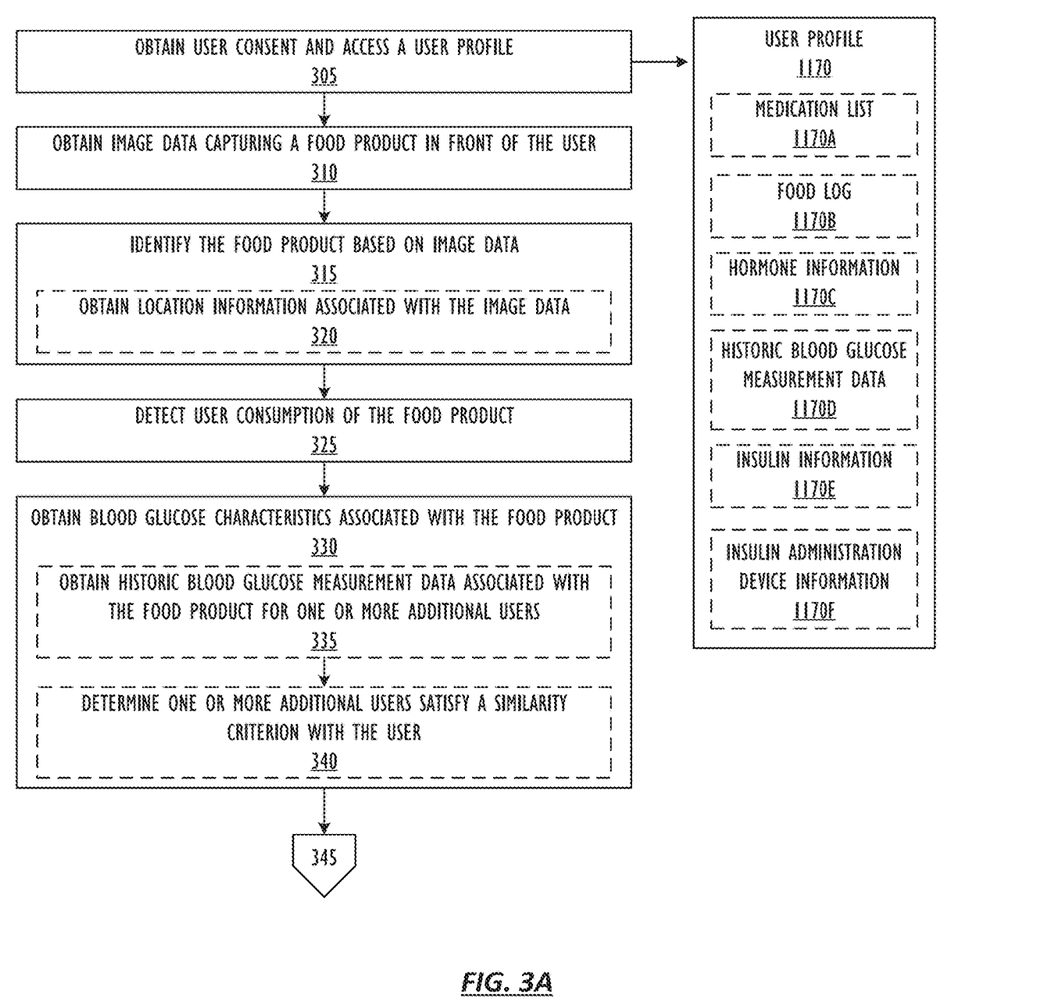
FIGS. 3A-B show, in flow chart form, a further method for improving blood glucose management, according to one or more embodiments.
Figure 3B:
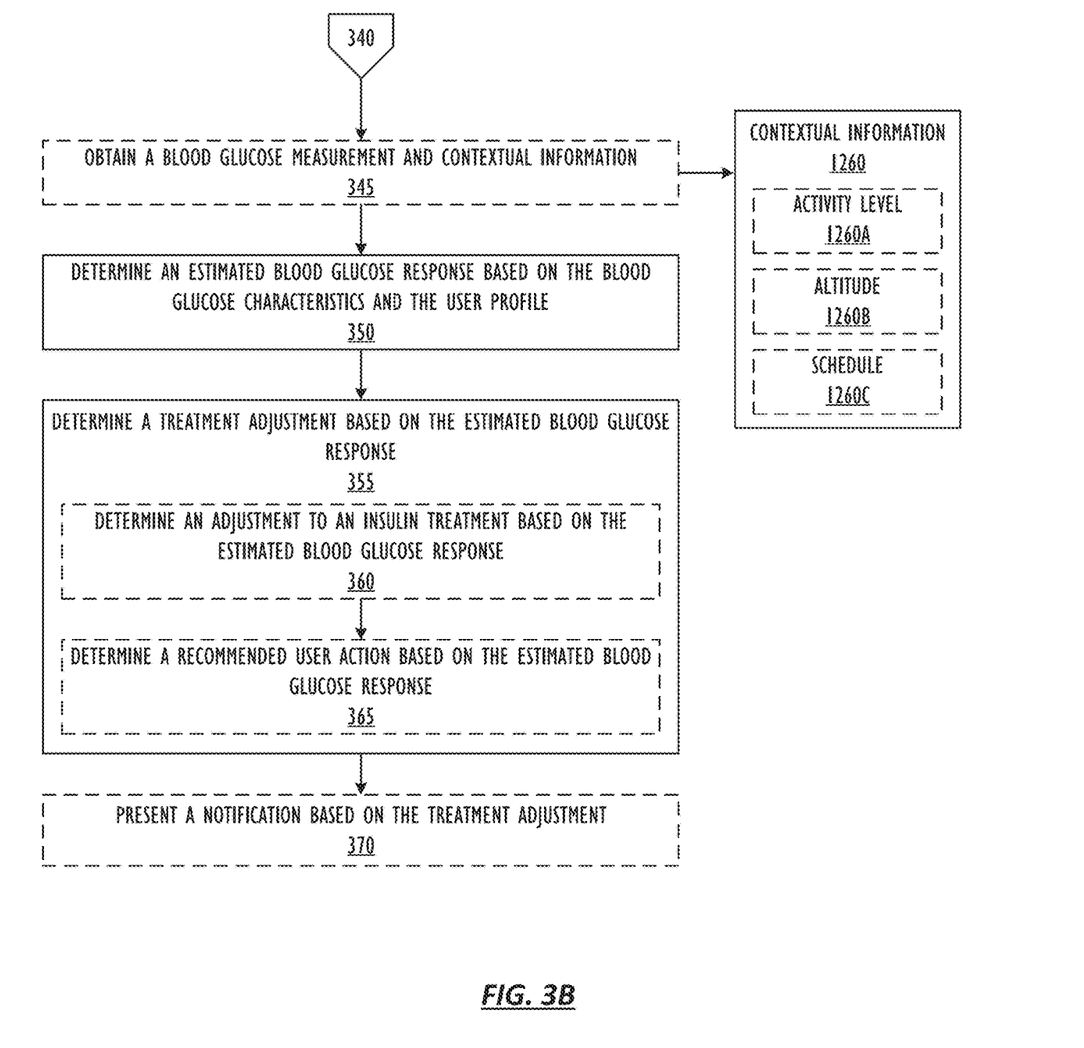

FIGS. 3A-B show, in flow chart form, a further method for improving blood glucose management. In one or more embodiments, certain actions take place as part of identifying the food product while other actions take place as part of obtaining blood glucose characteristics associated with the food product or determining a treatment adjustment based on the estimated blood glucose response. Still other actions comprise additional functionality. However, the various actions may take place in other locations within the flow chart of FIG. 2. For purposes of explanation, the following steps will be described in the context of FIG. 1. However, it should be understood that the various actions may be taken by alternate components. In addition, the various actions may be performed in a different order. Further, some actions may be performed simultaneously, and some may not be required, or others may be added.

The flow chart begins at 305 in FIG. 3A and blood glucose management module 1150 obtains a user's informed consent to access user profile 1170. In this example, user profile 1170 includes a medication list 1170A; a food log 1170B, such as from a diet journal or other application utilized to track food eaten; hormone information 1170C, for example information indicating the user is pregnant and corresponding pregnancy hormones; historic blood glucose measurement data 1170D for the user, such as from a glucose monitor included in sensors 1115; insulin information 1170E, such as the types and amounts of insulin available to the user from an insulin administration device, such as an insulin pump; and insulin administration device information 1170F, such as the capabilities of an insulin pump available to the user to administer insulin over a period of time, insulin pens, or single use insulin syringes. The flow chart continues at 310, where blood glucose management module 1150 obtains image data capturing a food product in front of the user, such as from camera 1110. As described above, the image data may include location data.

At 315, blood glucose management module 1150 identifies the food product based on image data. Identifying the food product may optionally further comprise step 320. At 320, blood glucose management module 1150 obtains location information associated with the image data. The location information may be obtained, for example, based on GPS information from a GPS sensor included in sensors 1115, network connection information, and the like. Location information may include, for example, a physical location of the electronic device, and/or contextual information, such as whether the device is in a particular restaurant or other establishment, or is at home, or the like. Recall blood glucose management module 1150 may work in conjunction with object detection module 1160 to identify the food product. In one or more embodiments, a machine learning algorithm is used to identify the food product. As discussed previously, the location information may be utilized to identify a restaurant such that blood glucose management module 1150 may base the food product identification on the restaurant's menu. Further, the location information may be used to distinguish between a commercial and a residential location so as to better determine whether an identified food product is homemade or commercially prepared.

The flow chart continues at 325, where blood glucose management module 1150 detects user consumption of the food product. Then, at 330, blood glucose management module 1150 obtains blood glucose characteristics associated with the food product. Obtaining blood glucose characteristics associated with the food product may optionally further comprise steps 335 and 340. At step 335, blood glucose management module 1150 obtains historic blood glucose measurement data associated with the food product for one or more additional users, for example from glucose characteristics database 1370. As discussed previously, in one or more embodiments glucose characteristics database 1370 may include historic blood glucose measurement data associated with the food product for one or more additional users. For example, glucose characteristics database 1370 may be a crowd-sourced database of additional users' anonymized user profiles and their blood glucose measurements associated with food products. Obtaining blood glucose characteristics may end at step 340, where blood glucose management module 1150 determines one or more additional users from the additional users included in glucose characteristics database 1370 satisfy a similarity criterion with the user. For example, blood glucose management module 1150 may exclude additional users of a different gender than the user or with an age difference greater than a threshold age difference. For another example, blood glucose management module 1150 may exclude additional users of the same gender as the user or with an age difference less than the threshold age difference in response to determining that the additional users have dissimilar blood glucose response to food products as the user, for example when historical blood glucose measurements for a particular food product for the additional users differ from historical blood glucose measurements for the particular food product for the user. Blood glucose management module 1150 excludes additional users dissimilar to the user such that the obtained blood glucose characteristics associated with the food product are based on additional users with similar characteristics as the user. In some embodiments, blood glucose management module 1150 works in conjunction with treatment planning module 1380 to determine one or more additional users satisfy the similarity criterion with the user.

The flow chart continues at 345 in FIG. 3B, where blood glucose management module 1150 may obtain a blood glucose measurement for the user and contextual information. In some embodiments, blood glucose management module 1150 obtains the user's informed permission to obtain the blood glucose measurement and access the contextual information. In some embodiments, blood glucose management module 1150 obtains the blood glucose measurement from a glucose monitor included in sensors 1115 in electronic device 1100 or sensors 1210 in electronic device 1200. In some embodiments, blood glucose management module 1150 obtains contextual information from contextual information 1260. In this example, contextual information 1260 includes the user's activity level 1260A from a heart rate monitor, altitude 1260B from an altimeter, and schedule 1260C from a calendar application included in memory 1140 in electronic device 1100 or memory 1240 in electronic device 1200 to determine the user's expected activity level or expected altitude for a certain period of time after the current time. Then, at 350, blood glucose management module 1150 determines an estimated blood glucose response based on the blood glucose characteristics, user profile 1170, the blood glucose measurement for the user, and contextual information 1260.

The flow chart continues at 355, where blood glucose management module 1150 determines a treatment adjustment based on the estimated blood glucose response. Determining a treatment adjustment may optionally further comprise steps 360 and 365. At 360, blood glucose management module 1150 determines an adjustment to an insulin treatment based on the estimated blood glucose response. For example, where user profile 1170 indicates the user has access to an insulin pump and insulin, blood glucose management module 1150 may determine a first rate and duration of administration, a basal rate of insulin administration, and a second rate and duration of administration, a bolus insulin administration. For example, the bolus insulin administration includes a larger amount of insulin to be administered over a shorter period of time while the basal rate insulin administration includes a smaller amount of insulin to be administered over a longer period of time. For another example, blood glucose management module 1150 may determine a first time for a first bolus administration and a second time for a second bolus administration in response to the estimated blood glucose response indicating increased blood glucose levels for the user for a time period longer than the insulin administered in the first bolus administration is effective. Next, at 365, blood glucose management module 1150 determines a recommended user action based on the estimated blood glucose response. For example, where user profile 1170 indicates the user has access to insulin pens, blood glucose management module 1150 may determine a particular time it is recommended the user administer insulin from an insulin pen. The flow chart continues with 370, where blood glucose management module 1150 presents a notification based on the treatment adjustment. In one or more embodiments, blood glucose management module 1150 may present the notification as an audio, tactile, or visual notification. For example, the notification may be read out to the user or shown on a display using I/O device 1120. Further, if the estimated blood glucose response exceeds a predetermined threshold, I/O device 1120 may vibrate electronic device 1100, or otherwise present feedback to the user. The user profile 1170, detection of user consumption of the food product, obtained blood glucose measurement for the user, contextual information 1260, estimated blood glucose response, adjustment to the insulin treatment, and the recommended user action may be considered health data for the user, subject to federal and/or state privacy law and health laws such as HIPAA. Blood glucose management module 1150 may implement appropriate privacy protections to secure the health data and require explicit informed permission from the user to share the health data with others.

Figure 4:
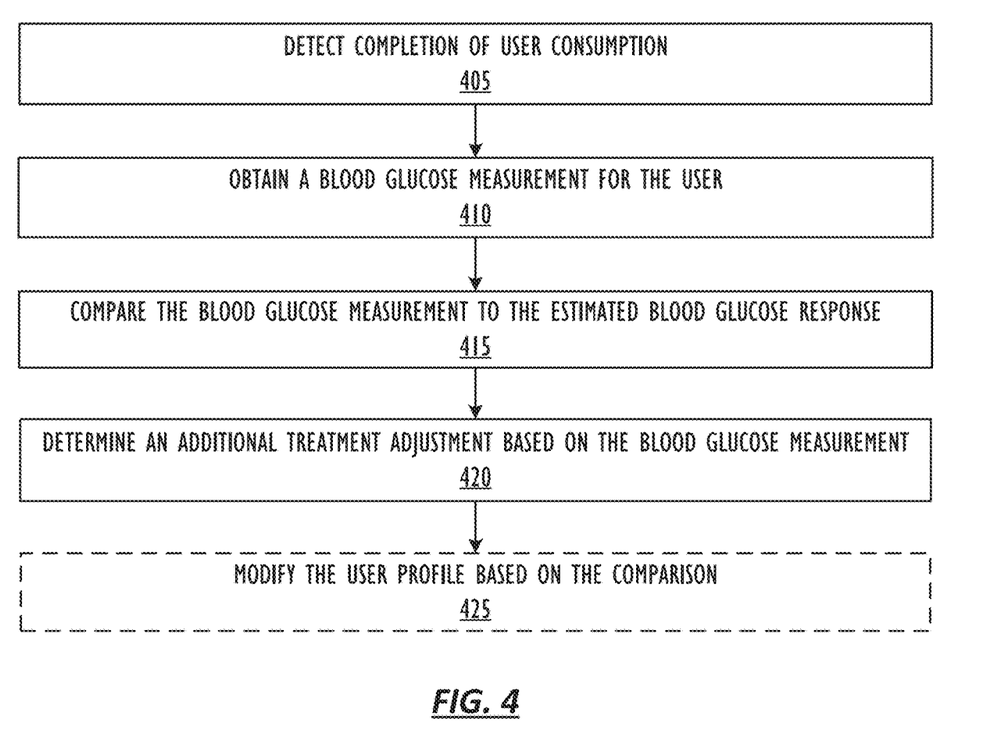
FIG. 4 shows, in flow chart form, a method for determining an additional treatment adjustment, according to one or more embodiments.

FIG. 4 shows, in flow chart form, an example method for determining an additional treatment adjustment, according to one or more embodiments. For purposes of explanation, the following steps will be described in the context of FIG. 1. However, it should be understood that the various actions may be taken by alternate components. In addition, the various actions may be performed in a different order. Further, some actions may be performed simultaneously, and some may not be required, or others may be added. The method for determining an additional treatment adjustment is performed after blood glucose management module 1150 performs a method to determine a treatment adjustment based on an estimated blood glucose response, such as those described in FIG. 2 and FIG. 3. The flow chart begins at 405, where blood glucose management module 1150 detects completion of user consumption. Blood glucose management module 1150 may work in conjunction with the microphone 1105, cameras 1110, sensors 1115, or some combination thereof. In one or more embodiments, for example, microphone 1105 may be used to detect the cessation of user chewing.

The flow chart continues at 410, where blood glucose management module 1150 obtains a blood glucose measurement for the user, such as from a glucose monitor included in sensors 1115. In some embodiments, blood glucose management module 1150 obtains the user's informed consent to obtain the blood glucose measurement. Next, at 415, blood glucose management module 1150 compares the blood glucose measurement to the estimated blood glucose response. At 420, blood glucose management module 1150 determines an additional treatment adjustment based on the comparison and the blood glucose measurement. For example, if the blood glucose measurement is higher than the estimated blood glucose response, blood glucose management module 1150 determines an additional treatment adjustment based on the higher than estimated blood glucose measurement. The additional treatment adjustment may be an adjustment to an insulin treatment. For another example, if the blood glucose measurement is lower than the estimated blood glucose response, blood glucose management module 1150 determines an additional treatment adjustment, which may recommend the user eat a snack to increase blood glucose levels or decrease a basal rate of insulin administration. In some embodiments, blood glucose management module 1150 continues to step 425, where it modifies user profile 1170 based on the comparison between the blood glucose measurement and the estimated blood glucose response. In some embodiments, blood glucose management module 1150 obtains the user's informed permission to modify user profile 1170. In one or more embodiments, modifying user profile 1170 may include updating the historic blood glucose measurement data for the food product.

Figure 5:
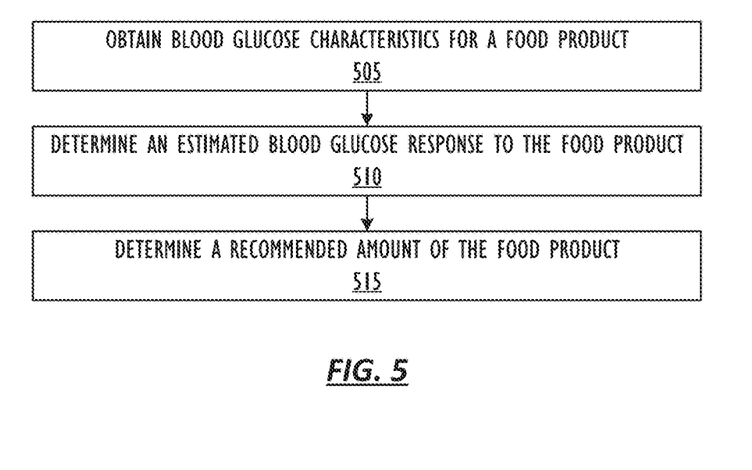
FIG. 5 shows, in flow chart form, a method for determining a recommended user action, according to one or more embodiments.

FIG. 5 shows, in flow chart form, a method for determining a recommended user action, according to one or more embodiments. For purposes of explanation, the following steps will be described in the context of FIG. 1. However, it should be understood that the various actions may be taken by alternate components. In addition, the various actions may be performed in a different order. Further, some actions may be performed simultaneously, and some may not be required, or others may be added. The method for determining a recommended user action may be performed by blood glucose management module 1150 as part of determining a treatment adjustment based on an estimated blood glucose response, such as those described in step 235 of FIG. 2, step 365 of FIG. 3, and step 420 of FIG. 4. The flowchart begins at 505, where blood glucose management module 1150 obtains blood glucose characteristics for a food product. As described previously herein with reference to FIGS. 2 and 3, in some embodiments blood glucose management module 1150 may obtain blood glucose characteristics from glucose characteristics database 1370. In some embodiments, the food product is included in user profile 1170 as an emergency blood sugar snack the user carries. The flowchart continues at 510, where blood glucose management module 1150 determines an estimated blood glucose response to the food product. For example, blood glucose management module 1150 determines the food product will increase the user's blood glucose level. Then, at 515, blood glucose management module 1150 determines a recommended amount of the food product. For example, blood glucose management module 1150 determines a particular amount of the food product will increase the user's blood glucose level to within an acceptable range.

Figure 6:
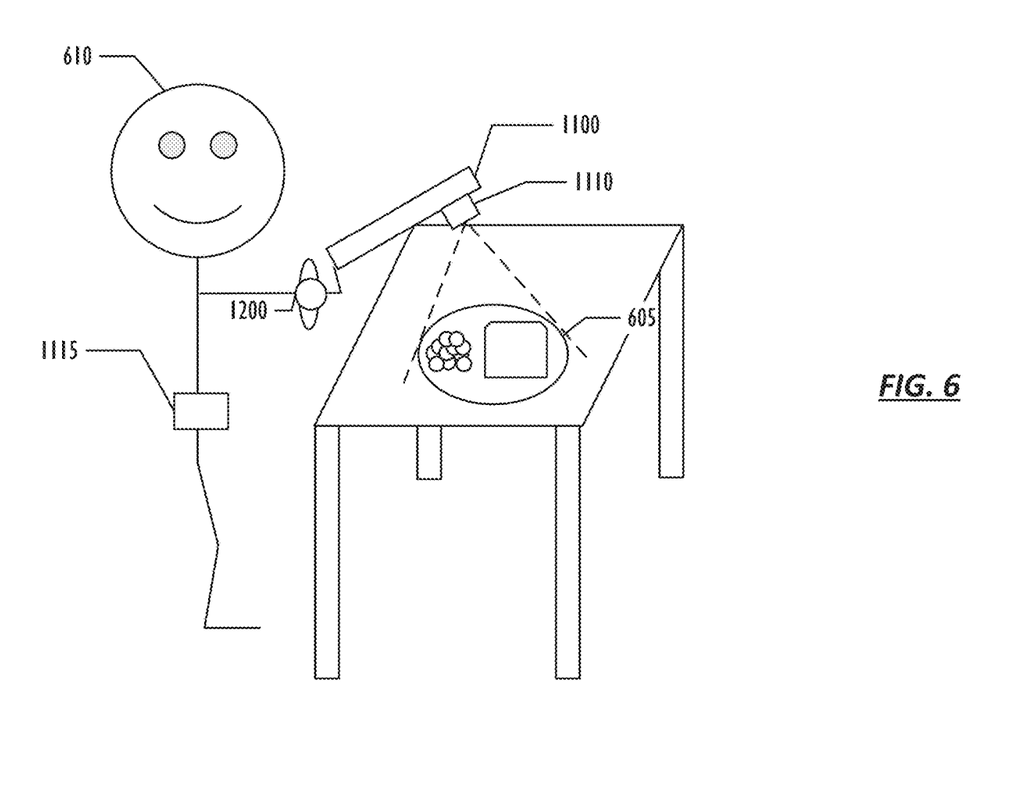
FIG. 6 shows, in system diagram form, an example setup of using an electronic device to improve blood glucose management in conjunction with a secondary electronic device, according to one or more embodiments.

Referring now to FIG. 6, a system diagram is shown for an example setup for improving blood glucose management, according to one or more embodiments. FIG. 6 shows a user 610 utilizing an electronic device 1100 to improve blood glucose management according to one or more embodiments. Electronic device 1100 uses camera 1110 to obtain image data of food product 605. In some embodiments, camera 1110 and I/O device 1120 are incorporated into glasses the user 610 may wear, for example as part of a head mounted device or system. In this example, sensors 1115 include an insulin pump and a glucose monitor. Electronic device 1100 is connected to secondary electronic device 1200, here a smartwatch, via Bluetooth. In this embodiment, secondary electronic device 1200 includes a heart monitor in sensors 1210.

In one or more embodiments, user profile 1170 may be stored locally or remotely, for example in network storage. In one or more embodiments, the system may also be used for meal planning. As an example, in response to determining that a time for a particular meal is approaching or has arrived, the system may present food options and corresponding treatment adjustments. For example, the system may present a particular food option and recommend a particular insulin dose before eating the particular food option. The food options may be determined, for example, based on geographic data. As an example, GPS data may be used to locate nearby restaurants, and historic data regarding food consumption may be utilized to identify food options available nearby. Further, in one or more embodiments, the food options may be presented in an order that is determined, for example, by historic blood glucose response for a particular meal or the like.

Figure 7:
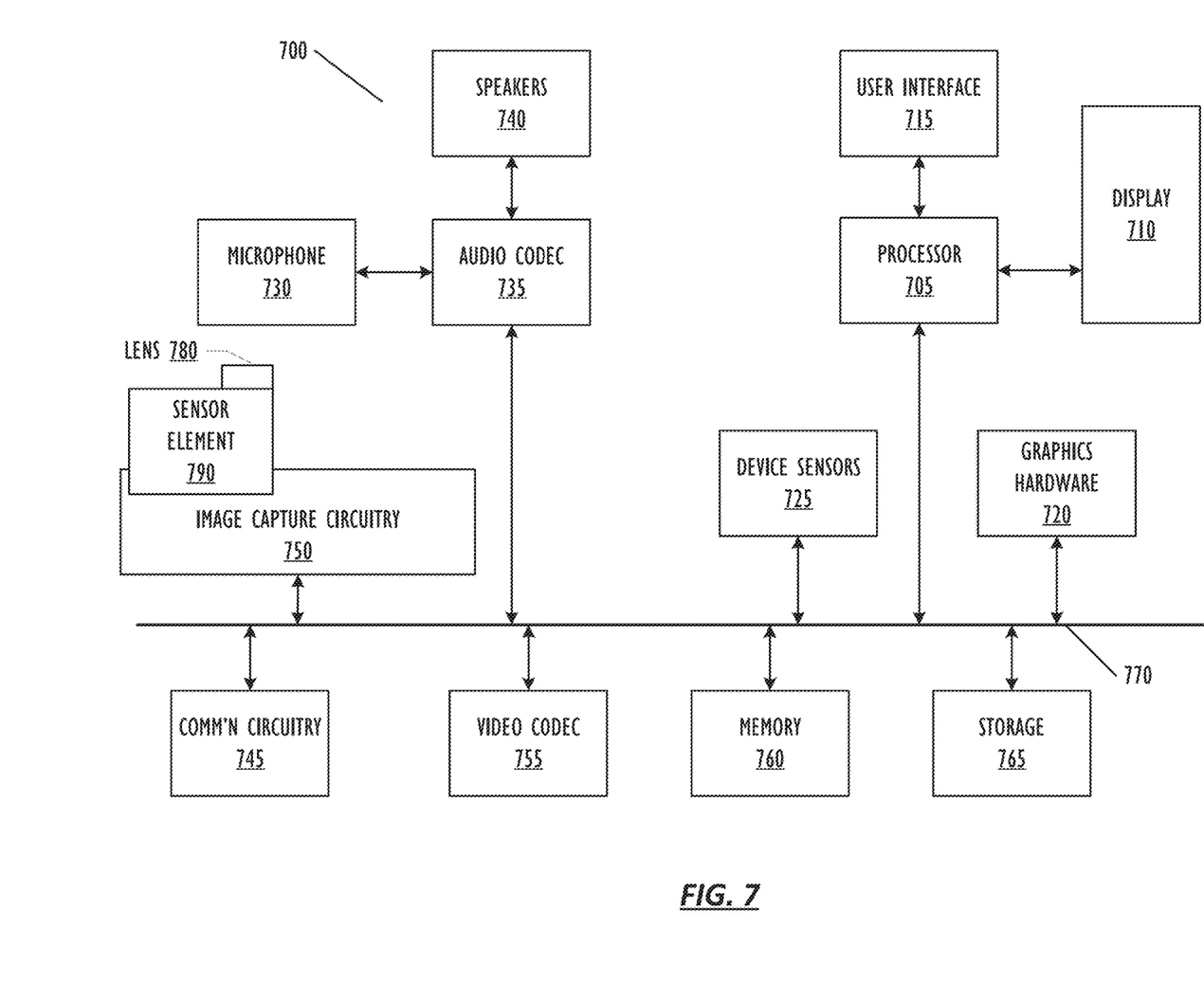
FIG. 7 shows, in block diagram form, a simplified multifunctional electronic device according to one or more embodiments.

Referring now to FIG. 7, a simplified functional block diagram of illustrative multifunction device 700 is shown according to one embodiment. Multifunction electronic device 700 may include processor 705, display 710, user interface 715, graphics hardware 720, device sensors 725 (e.g., proximity sensor/ambient light sensor, accelerometer and/or gyroscope), microphone 730, audio codec(s) 735, speaker(s) 740, communications circuitry 745, digital image capture circuitry 750, video codec(s) 755 (e.g., in support of digital image capture unit 750), memory 760, storage device 765, and communications bus 770. Multifunction electronic device 700 may be, for example, a personal electronic device such as a personal digital assistant (PDA), mobile telephone, or a tablet computer.

Processor 705 may execute instructions necessary to carry out or control the operation of many functions performed by device 700 (e.g., such as the determination of an estimated blood glucose response as disclosed herein). Processor 705 may, for instance, drive display 710 and receive user input from user interface 715. User interface 715 may allow a user to interact with device 700. For example, user interface 715 can take a variety of forms, such as a button, keypad, dial, a click wheel, keyboard, display screen and/or a touch screen. Processor 705 may also, for example, be a system-on-chip such as those found in mobile devices and include a dedicated graphics processing unit (GPU). Processor 705 may be based on reduced instruction-set computer (RISC) or complex instruction-set computer (CISC) architectures or any other suitable architecture and may include one or more processing cores. Graphics hardware 720 may be special purpose computational hardware for processing graphics and/or assisting processor 705 to process graphics information. In one embodiment, graphics hardware 720 may include a programmable GPU.

Image capture circuitry 750 may include lens 780. Lens assembly may have an associated sensor element 790. Image capture circuitry 750 may capture still and/or video images. Output from image capture circuitry 750 may be processed, at least in part, by video codec(s) 755 and/or processor 705 and/or graphics hardware 720, and/or a dedicated image processing unit or pipeline incorporated within circuitry 755. Images so captured may be stored in memory 760 and/or storage 765. Microphone 730 may capture audio recordings that may be processed in accordance with this disclosure, at least in part, by audio codec(s) 735 and/or processor 705. Audio recordings so captured may be stored in memory 760 and/or storage 765.

Memory 760 may include one or more different types of media used by processor 705 and graphics hardware 720 to perform device functions. For example, memory 760 may include memory cache, read-only memory (ROM), and/or random access memory (RAM). Storage 765 may store media (e.g., audio, image and video files), computer program instructions or software, preference information, device profile information, and any other suitable data. Storage 765 may include one more non-transitory storage mediums including, for example, magnetic disks (fixed, floppy, and removable) and tape, optical media such as CD-ROMs and digital video disks (DVDs), and semiconductor memory devices such as Electrically Programmable Read-Only Memory (EPROM), and Electrically Erasable Programmable Read-Only Memory (EEPROM). Memory 760 and storage 765 may be used to tangibly retain computer program instructions or code organized into one or more modules and written in any desired computer programming language. When executed by, for example, processor 705 such computer program code may implement one or more of the methods described herein.

As described above, one aspect of the present technology is the gathering and use of data available from various sources to improve management of blood glucose levels and blood glucose treatment. The present disclosure contemplates that in some instances, this gathered data may include personal information data that uniquely identifies or can be used to contact or locate a specific person. Such personal information data can include demographic data, location-based data, telephone numbers, email addresses, twitter ID's, home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to deliver targeted content that is of greater interest to the user. Accordingly, use of such personal information data enables users to calculate control of the delivered content. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

The scope of the disclosed subject matter should be determined with reference to the appended claims, along with the full scope of equivalents to which such claims are entitled. In the appended claims, the terms "including" and "in which" are used as the plain-English equivalents of the respective terms "comprising" and "wherein."

The invention claimed is:

1. A method for improving blood glucose management, comprising:
   obtaining a user profile comprising health information for a user;
   obtaining, from a camera, image data capturing a food product in front of the user;
   identifying the food product based on the image data;
   detecting user consumption of the food product;
   obtaining blood glucose characteristics associated with the food product from a characteristics data store comprising anonymized health information for additional users and corresponding historical blood glucose measurements associated with the food product for the additional users;
   determining an estimated blood glucose response based on the anonymized health information, the historical blood glucose characteristics associated with the food product of additional users, and the user profile; and
   determining a treatment adjustment based on the estimated blood glucose response.

2. The method of claim 1, wherein determining the treatment adjustment comprises one of:
   determining an insulin dose, and
   determining a recommended user action.

3. The method of claim 1, wherein the estimated blood glucose response is determined based on historical blood glucose measurements associated with the food product for additional users based on a similarity criterion.

4. The method of claim 3, wherein the similarity criterion is determined based on a similarity between an age, weight, and gender of the user and the additional users.

5. The method of claim 3, wherein the similarity criterion is determined based on a similarity between the blood glucose responses to food products between the user and the additional users.

6. The method of claim 1, further comprising obtaining a blood glucose measurement for the user from a glucose monitor and contextual information, wherein the treatment adjustment is further based on the blood glucose measurement and the contextual information.

7. The method of claim 1, further comprising:
   detecting completion of the user consumption;
   obtaining a blood glucose measurement from a blood glucose monitor in response to detecting the completion of the user consumption;
   comparing the blood glucose measurement to the estimated blood glucose response; and
   determining an additional treatment adjustment based on the blood glucose measurement.

8. The method of claim 7, further comprising modifying the user profile based on the comparing.

9. The method of claim 8, further comprising sharing blood glucose data of the user profile with the characteristics data store.

10. A system, comprising:
    one or more cameras;
    one or more processors; and
    one or more computer readable media comprising computer readable instructions executable by the one or more processors to:
    obtain a user profile, comprising health information for a user;
    obtain, by the one or more cameras, image data capturing a food product in front of the user;
    identify the food product based on the image data;
    detect user consumption of the food product;
    obtain blood glucose characteristics associated with the food product from a characteristics data store comprising anonymized health information for additional users and corresponding historical blood glucose measurements associated with the food product for the additional users;
    determine an estimated blood glucose response based on the anonymized health information, the historical blood glucose characteristics associated with the food product of additional users, and the user profile; and
    determine a treatment adjustment based on the estimated blood glucose response.

11. The system of claim 10, wherein the estimated blood glucose response is determined based on historical blood glucose measurements associated with the food product for additional users based on a similarity criterion.

12. The system of claim 11, wherein the similarity criterion is determined based on a similarity between an age, weight, and gender of the user and the additional users.

13. The system of claim 11, wherein the similarity criterion is determined based on a similarity between the blood glucose responses to food products between the user and the additional users.

14. The system of claim 10, wherein the one or more computer readable media further comprise computer readable instructions to:
   detect completion of the user consumption;
   obtain a blood glucose measurement in response to detecting the completion of the user consumption;
   compare the blood glucose measurement to the estimated blood glucose response; and
   determine an additional treatment adjustment based on the blood glucose measurement.

15. The system of claim 14, wherein the computer readable media further comprise computer readable instructions to modify the user profile based on the comparison between the blood glucose measurement and the estimated blood glucose response.

16. The system of claim 10, wherein the computer readable media further comprise computer readable instructions to share blood glucose data of the user profile with the characteristics data store.

17. A non-transitory machine readable medium comprising instructions executable by one or more processors to:
   obtain a user profile comprising health information for a user;
   obtain, from a camera, image data capturing a food product in front of the user;
   identify the food product based on the image data;
   detect user consumption of the food product;
   obtain blood glucose characteristics associated with the food product from a characteristics data store comprising anonymized health information for additional users and corresponding historical blood glucose measurements associated with the food product for the additional users;
   determine an estimated blood glucose response based on the anonymized health information, the historical blood glucose characteristics associated with the food product of additional users, and the user profile; and
   determine a treatment adjustment based on the estimated blood glucose response.

18. The non-transitory machine readable medium of claim 17, wherein the estimated blood glucose response is determined based on historical blood glucose measurements associated with the food product for additional users based on a similarity criterion.

19. The non-transitory machine readable medium of claim 18, wherein the similarity criterion is determined based on a similarity between an age, weight, and gender of the user and the additional users.

20. The non-transitory machine readable medium of claim 17, further comprising instructions to:
   detect completion of the user consumption;
   obtain a blood glucose measurement in response to detecting completion of the user consumption;
   compare the blood glucose measurement to the estimated blood glucose response; and
   determine an additional treatment adjustment based on the blood glucose measurement.

21. The non-transitory machine readable medium of claim 20, further comprising instructions to modify the user profile based on the comparison.

22. The non-transitory machine readable medium of claim 17, further comprising instructions to share blood glucose data of the user profile with the characteristics data store.

23. The non-transitory machine readable medium of claim 17, wherein the similarity criterion is determined based on a similarity between the blood glucose responses to food products between the user and the additional users.

* * * * *